US007256007B2

(12) United States Patent
Nicholson et al.

(10) Patent No.: US 7,256,007 B2
(45) Date of Patent: Aug. 14, 2007

(54) METHODS OF REGULATING CYTOKINE SIGNALLING

(75) Inventors: Sandra Elaine Nicholson, Newport (AU); Manuel Baca, Viewbank (AU); Nicos A. Nicola, Mont Albert (AU); Douglas Hilton, Warrandyte (AU); Jian Guo Zhang, North Melbourne (AU); Louis Fabri, Diamond Creek (AU); Andrew Nash, Kew (AU)

(73) Assignee: The Walter and Eliza Hall Institute of Medical Research, Victoria (AU)

( * ) Notice: Subject to any disclaimer, the term of this patent is extended or adjusted under 35 U.S.C. 154(b) by 679 days.

(21) Appl. No.: 10/221,125

(22) PCT Filed: Mar. 9, 2001

(86) PCT No.: PCT/AU01/00263

§ 371 (c)(1),
(2), (4) Date: Feb. 19, 2003

(87) PCT Pub. No.: WO01/66128

PCT Pub. Date: Sep. 13, 2001

(65) Prior Publication Data

US 2003/0191058 A1    Oct. 9, 2003

(30) Foreign Application Priority Data

Mar. 9, 2000  (AU) ................... PQ6147

(51) Int. Cl.
G01N 33/53 (2006.01)
G01N 33/00 (2006.01)
C07K 1/00 (2006.01)
C07K 14/00 (2006.01)

(52) U.S. Cl. ............ 435/7.8; 435/7.92; 530/350; 530/402

(58) Field of Classification Search .......... None
See application file for complete search history.

(56) References Cited

FOREIGN PATENT DOCUMENTS

WO    WO 99/40946    8/1999
WO    WO 00/63357    10/2000

OTHER PUBLICATIONS

Hibi et al. 1990. Cell 63:1149-1157.*
Warren et al. 1999. J Leuk Bio. 66:588-592.*
Kim et al. 1996. J Biol Chem. 271:20690-20698.*
Wills, 1990, Biochemistry 29:8509-8517.*
Ngo et al., 1994, The Protein Folding Problem and Tertiary Structure Prediction, pp. 492-495.*
Starr R. et al., "A Family of Cytokine-Inducible Inhibitors of Signalling", *Nature* 387:917-921 (1997).
Nicola N.A. et al., "The Suppressors of Cytokine Signaling (SOCS) Proteins: Important Feedback Inhibitors of Cytokine Action", *Experimental Hematology* 28:1105-1112 (2000).
Bjorbaek C. et al., SOCS3 Mediates Feedback Inhibition of the Leptin Receptor Via Tyr$^{985}$, *The Journal of Biological Chemistry* 275(51):40649-40657 (2000).
Sasaki A. et al., CIS3/SOCS-3 Suppresses Erythropoietin (EPO) Signaling by Binding the EPO Receptor and JAK2, *The Journal of Biological Chemistry* 275(38):29338-29347 (2000).
Terstegen L. et al., "The Inhibition of Interleukin-6-Dependent STAT Activation by Mitogen-Activated Protein Kinases Depends on Tyrosine 759 in the Cytoplasmic Tail of Glycoprotein 130", *The Journal of Biological Chemistry* 275(25):18810-18817 (2000).
Nicholson S.E. et al., "Suppressor of Cytokine Signaling-3 Preferentially Binds to the SHP-2-Binding Site on the Shared Cytokine Receptor Subunit GP 130", *PNAS* 97(12):6493-6498 (2000).
Eyckerman S et al., "Identification of the Y985 and Y1077 Motifs as SOCS3 Recruitment Sites in the Murine Leptin Receptor", *FEBS Letter* 486:33-37 (2000).
Krebs D.L. et al., "SOCS: Physiological Suppressors of Cytokine Signaling", *Journal of Cell Science* 113:2813-2819 (2000).

\* cited by examiner

*Primary Examiner*—Eileen O'Hara
*Assistant Examiner*—Shulamith H. Shafer
(74) *Attorney, Agent, or Firm*—Scully, Scott, Murphy & Presser, P.C.

(57) ABSTRACT

The present invention relates generally to a method for regulating cytokine signaling and agents useful for same. The method of the present invention is predicated in part on the identification of the molecular target of suppressor of cytokine signaling (SOCS) interaction in controlling cytokine signaling. The identification of the molecular target permits the development of assays to screen for a range of agonists and antagonists useful in modulating cytokine function. The present invention further provides, therefore, screening assays and more particularly high through-put screening assays for agonists and antagonists of SOCS-receptor interaction. Such agonists and antagonists are useful in the manufacture of medicaments for controlling cytokine signaling. Control of cytokine signaling is important for the treatment of a range of conditions including cancer, inflammatory conditions, immunological disorders and any other conditions involving aberrations of signal transduction.

17 Claims, 8 Drawing Sheets

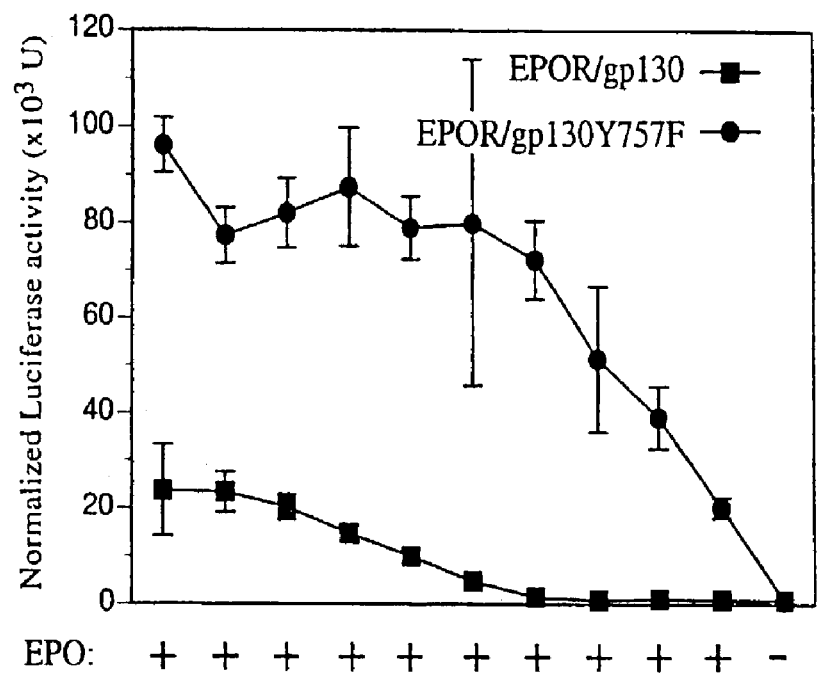
Figure 4D
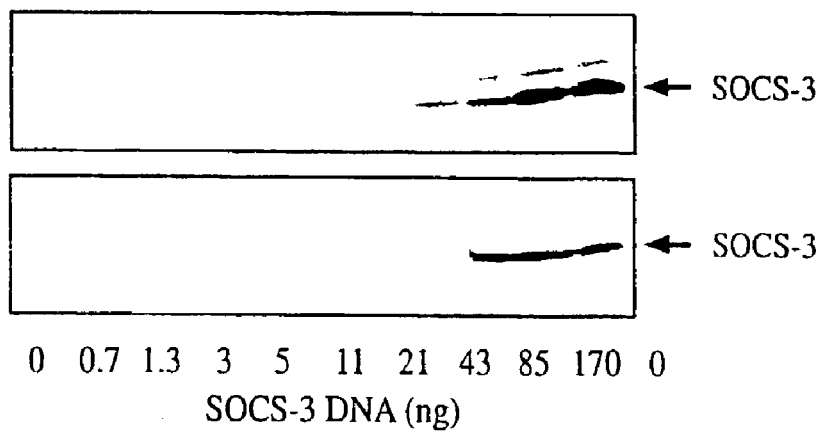
Figure 4E
Figure 4F

Comparison of gp130, leptin and EPO phosphopeptide binding sites

| | | |
|---|---|---|
| mgp130 | Y757 | STASTVEYSTVVHSG |
| hgp130 | Y757 | NTSSTVQYSTVVHSG |
| Leptin | Y985 | QRQPFVKYATLISNS |
| EPO | Y401 | ASAASFEYTILDPSS |

Figure 5

SEQUENCE LISTING

```
<160> NUMBER OF SEQ ID NOS: 30

<210> SEQ ID NO 1
<211> LENGTH: 14
<212> TYPE: PRT
<213> ORGANISM: Mus musculus

<400> SEQUENCE: 1

Ile Glu Thr Asp Lys Glu Tyr Thr Val Lys Asp Asp Arg Asp
1               5                   10

<210> SEQ ID NO 2
<211> LENGTH: 14
<212> TYPE: PRT
<213> ORGANISM: Mus musculus

<400> SEQUENCE: 2

Leu Pro Gln Asp Lys Glu Tyr Lys Val Lys Glu Pro Gly Glu
1               5                   10

<210> SEQ ID NO 3
<211> LENGTH: 14
<212> TYPE: PRT
<213> ORGANISM: Mus musculus

<400> SEQUENCE: 3

Leu Pro Leu Gly Lys Asp Tyr Val Val Arg Glu Pro Gly Gln
1               5                   10

<210> SEQ ID NO 4
<211> LENGTH: 15
<212> TYPE: PRT
<213> ORGANISM: Mus musculus

<400> SEQUENCE: 4

Ser Thr Ala Ser Thr Val Glu Tyr Ser Thr Val Val His Ser Gly
1               5                   10                  15
```

<210> SEQ ID NO 5
<211> LENGTH: 15
<212> TYPE: PRT
<213> ORGANISM: Homo sapiens

<400> SEQUENCE: 5

Asn Thr Ser Ser Thr Val Gln Tyr Ser Thr Val Val His Ser Gly
1               5                   10                  15

<210> SEQ ID NO 6
<211> LENGTH: 15
<212> TYPE: PRT
<213> ORGANISM: Homo sapiens

<400> SEQUENCE: 6

Gln Arg Gln Pro Phe Val Lys Tyr Ala Thr Leu Ile Ser Asn Ser
1               5                   10                  15

<210> SEQ ID NO 7
<211> LENGTH: 15
<212> TYPE: PRT
<213> ORGANISM: Homo sapiens

<400> SEQUENCE: 7

Ala Ser Ala Ala Ser Phe Glu Tyr Thr Ile Leu Asp Pro Ser Ser
1               5                   10                  15

<210> SEQ ID NO 8
<211> LENGTH: 15
<212> TYPE: PRT
<213> ORGANISM: Mus musculus

<400> SEQUENCE: 8

Ser Thr Ala Ser Thr Val Glu Tyr Ser Thr Val Val His Ser Gly
1               5                   10                  15

<210> SEQ ID NO 9
<211> LENGTH: 15
<212> TYPE: PRT
<213> ORGANISM: Mus musculus

<400> SEQUENCE: 9

Ser Thr Ala Ser Thr Val Glu Tyr Ala Thr Val Val His Ser Gly
1               5                   10                  15

<210> SEQ ID NO 10
<211> LENGTH: 15
<212> TYPE: PRT
<213> ORGANISM: Mus musculus

<400> SEQUENCE: 10

Ser Thr Ala Ser Thr Val Glu Tyr Ser Ala Val Val His Ser Gly
1               5                   10                  15

<210> SEQ ID NO 11
<211> LENGTH: 15
<212> TYPE: PRT
<213> ORGANISM: Mus musculus

<400> SEQUENCE: 11

Ser Thr Ala Ser Thr Val Glu Tyr Ser Thr Ala Val His Ser Gly
1               5                   10                  15

```
<210> SEQ ID NO 12
<211> LENGTH: 15
<212> TYPE: PRT
<213> ORGANISM: Mus musculus

<400> SEQUENCE: 12

Ser Thr Ala Ser Thr Val Glu Tyr Ser Thr Val Ala His Ser Gly
1               5                   10                  15

<210> SEQ ID NO 13
<211> LENGTH: 15
<212> TYPE: PRT
<213> ORGANISM: Mus musculus

<400> SEQUENCE: 13

Ser Thr Ala Ser Thr Val Glu Tyr Ser Thr Val Val Ala Ser Gly
1               5                   10                  15

<210> SEQ ID NO 14
<211> LENGTH: 15
<212> TYPE: PRT
<213> ORGANISM: Mus musculus

<400> SEQUENCE: 14

Ser Thr Ala Ser Thr Val Glu Tyr Ser Thr Val Val His Ser Gly
1               5                   10                  15

<210> SEQ ID NO 15
<211> LENGTH: 14
<212> TYPE: PRT
<213> ORGANISM: Mus musculus

<400> SEQUENCE: 15

Ser Thr Ala Ser Thr Val Glu Tyr Ser Thr Val Val His Ser
1               5                   10

<210> SEQ ID NO 16
<211> LENGTH: 13
<212> TYPE: PRT
<213> ORGANISM: Mus musculus

<400> SEQUENCE: 16

Ser Thr Ala Ser Thr Val Glu Tyr Ser Thr Val Val His
1               5                   10

<210> SEQ ID NO 17
<211> LENGTH: 12
<212> TYPE: PRT
<213> ORGANISM: Mus musculus

<400> SEQUENCE: 17

Ser Thr Ala Ser Thr Val Glu Tyr Ser Thr Val Val
1               5                   10

<210> SEQ ID NO 18
<211> LENGTH: 11
<212> TYPE: PRT
<213> ORGANISM: Mus musculus

<400> SEQUENCE: 18

Thr Val Glu Tyr Ser Thr Val Val His Ser Gly
1               5                   10

<210> SEQ ID NO 19
<211> LENGTH: 10
```

<212> TYPE: PRT
<213> ORGANISM: Mus musculus

<400> SEQUENCE: 19

Val Glu Tyr Ser Thr Val Val His Ser Gly
1               5                   10

<210> SEQ ID NO 20
<211> LENGTH: 9
<212> TYPE: PRT
<213> ORGANISM: Mus musculus

<400> SEQUENCE: 20

Glu Tyr Ser Thr Val Val His Ser Gly
1               5

<210> SEQ ID NO 21
<211> LENGTH: 8
<212> TYPE: PRT
<213> ORGANISM: Mus musculus

<400> SEQUENCE: 21

Tyr Ser Thr Val Val His Ser Gly
1               5

<210> SEQ ID NO 22
<211> LENGTH: 10
<212> TYPE: PRT
<213> ORGANISM: Mus musculus

<400> SEQUENCE: 22

Ala Glu Tyr Ser Thr Val Val His Ser Gly
1               5                   10

<210> SEQ ID NO 23
<211> LENGTH: 10
<212> TYPE: PRT
<213> ORGANISM: Mus musculus

<400> SEQUENCE: 23

Val Ala Tyr Ser Thr Val Val His Ser Gly
1               5                   10

<210> SEQ ID NO 24
<211> LENGTH: 15
<212> TYPE: PRT
<213> ORGANISM: Mus musculus

<400> SEQUENCE: 24

Phe Asn Ser Lys Asp Gln Met Tyr Ser Asp Gly Asn Phe Thr Asp
1               5                   10                  15

<210> SEQ ID NO 25
<211> LENGTH: 15
<212> TYPE: PRT
<213> ORGANISM: Mus musculus

<400> SEQUENCE: 25

Ser Thr Val Val His Ser Gly Tyr Arg His Gln Val Pro Ser Val
1               5                   10                  15

<210> SEQ ID NO 26
<211> LENGTH: 15
<212> TYPE: PRT

-continued

```
<400> SEQUENCE: 26

Glu Ile Leu Pro Arg Gln Pro Tyr Phe Lys Gln Asn Cys Ser Gln
1               5                   10                  15

<210> SEQ ID NO 27
<211> LENGTH: 15
<212> TYPE: PRT
<213> ORGANISM: Mus musculus

<400> SEQUENCE: 27

Asp Glu Glu Ile Pro Lys Ser Tyr Leu Pro Gln Thr Val Arg Gln
1               5                   10                  15

<210> SEQ ID NO 28
<211> LENGTH: 11
<212> TYPE: PRT
<213> ORGANISM: Mus musculus

<400> SEQUENCE: 28

Gln Thr Val Arg Gln Gly Gly Tyr Met Pro Gln
1               5                   10

<210> SEQ ID NO 29
<211> LENGTH: 15
<212> TYPE: PRT
<213> ORGANISM: Mus musculus

<400> SEQUENCE: 29

Asp Asp Pro Lys Arg Thr Gly Tyr Ile Lys Thr Glu Leu Ile Ser
1               5                   10                  15

<210> SEQ ID NO 30
<211> LENGTH: 15
<212> TYPE: PRT
<213> ORGANISM: Mus musculus

<400> SEQUENCE: 30

Asp Pro Gly Ser Ala Ala Pro Tyr Leu Lys Thr Lys Phe Ile Ser
1               5                   10                  15
```

METHODS OF REGULATING CYTOKINE SIGNALLING

FIELD OF THE INVENTION

The present invention relates generally to a method for regulating cytokine signaling and agents useful for same. The method of the present invention is predicated in part on the identification of the molecular target of suppressor of cytokine signaling (SOCS) interaction in controlling cytokine signaling. The identification of the molecular target permits the development of assays to screen for a range of agonists and antagonists useful in modulating cytokine function. The present invention further provides, therefore, screening assays and more particularly high through-put screening assays for agonists and antagonists of SOCS-receptor interaction. Such agonists and antagonists are useful in the manufacture of medicaments for controlling cytokine signaling. Control of cytokine signaling is important for the treatment of a range of conditions including cancer, inflammatory conditions, immunological disorders and any other conditions involving aberrations of signal transduction.

BACKGROUND OF THE INVENTION

Reference to any prior art in this specification is not, and should not be taken as, an acknowledgment or any form of suggestion that this prior art forms part of the common general knowledge in Australia or any other country.

Bibliographic details of the publications referred to by author in this specification are collected at the end of the description.

Cytokines control a wide variety of biological responses, thus the duration and intensity of their effects must be tightly regulated. Upon stimulation by cytokine, specific cell surface receptors oligomerise and cause activation of the JAK-STAT signaling pathway (Heim, 1999; Ihle et al., 1998; Leonard and O'Shea, 1998). The transient nature of this signaling cascade is partly a consequence of the action of negative regulatory molecules such as SHP-1, PIAS-3 and the SOCS (suppressor of cytokine signaling) (alternate names SSI, JAB, CIS) proteins, each of which inhibit the JAK-STAT signaling pathway and ensure the appropriate level of response to a particular cytokine stimulus is maintained (Endo et al., 1997; Gisselbrecht, 1999; Hilton, 1999; Naka et al., 1997; Starr et al., 1997; Yoshimura, 1998).

The SOCS family of proteins comprises a number of members, including SOCS-1 through SOCS-7 and CIS, and the expression of several of these is known to be induced by cytokines (Hilton, 1999; Hilton et al., 1998; Yoshimura, 1998). SOCS-7 and CIS contain two regions of homology—a central SH2 domain and a C-terminal 40 amino acid motif known as the SOCS box. While the SOCS box acts to recruit elongins BC, a protein complex implicated in the proteasomal degradation pathway (Kamura et al., 1998; Zhang et al., 1999), the SH2 domains of the SOCS proteins are responsible for specific binding to activated (phosphorylated) signaling molecules and may also play a role in the mechanism of signal suppression. For instance, CIS binds via its SH2 domain to phosphorylated erythropoietin (EPO) and interleukin-3 (IL-3) receptors at the same sites used for STAT-5 binding, thus preventing docking and activation of this transcription factor (Matsumoto et al., 1997; Yoshimura et al., 1995). By contrast, the SH2 domain of SOCS-1 binds to activated JAKs, and together with the action of an additional protein interaction motif upstream of the SH2 domain, results in inhibition of the kinase catalytic activity (Nicholson et al., 1999; Sasaki et al., 1999).

A number of studies have identified cytokines which can induce the expression of SOCS-3 mRNA, including CNTF (Bjorback et al., 1999), LIF (Bousquet et al., 1999), IL-6 (Starr et al., 1997), IL-11 (Auernhammer and Melmed, 1999a), leptin (Bjorbaek et al., 1998), IL-2 (Cohney et al., 1999), IL-10 (Donnelly et al., 1999; Ito et al., 1999), prolactin (Pezet et a!., 1999), growth hormone (Adams et al., 1998) and insulin. Overexpression of SOCS-3 results in the inhibition of signaling by each of these cytokines, and under these conditions SOCS-3 has been shown to physically associate with either JAK kinase (Sasaki et al., 1999), or the receptors for growth hormone (Hansen et al., 1999), IL-2Rβ (Cohney et al., 1999), and insulin receptors. However, given that overexpression can lead to elevated protein levels at which non-specific interactions can result, it is difficult to assess whether all of these observations have a genuine biological relevance. Alternatively, gene knockout studies have shown that SOCS-3$^{-/-}$ mice die embryonically from a disease possibly associated with excessive foetal erythropoiesis (Marine et al., 1999).

Recently, it was proposed that the mechanism by which SOCS-3 inhibits signaling is identical to that of SOCS-1. As had been demonstrated for SOCS-1 (Yasukawa et al., 1999), SOCS-3 was also shown to associate with JAK2 in intact cells, and to a synthetic phosphopeptide encompassing the activation loop from JAK2 (Sasaki et al., 1999). The region of SOCS-3 immediately N-terminal to the SH2 domain has also been shown to be important for biological activity (Narazaki et al., 1998; Nicholson et al., 1999; Sasaki et al., 1999), and based on sequence similarity to SOCS-1, was also proposed to function as a kinase active site inhibitor. However, despite these similarities, there is evidence to suggest that the mechanism of signaling suppression used by SOCS-3 differs from that of SOCS-1. Unlike SOCS-1, SOCS-3 does not inhibit the catalytic activity of JAK1 or JAK2 in an in vitro kinase reaction (Nicholson et al., 1999). Furthermore, the kinetics of IL-6 signal suppression, as measured by inhibition of STAT3 phosphorylation, is considerably slower for SOCS-3 as compared to SOCS-1 (Suzuki et al., 1998). While forced expression of SOCS-1 in M1 cells results in rapid and total inhibition of STAT3 phosphorylation within 30 minutes, inhibition by SOCS-3 slowly increases over the course of several hours (Suzuki et al., 1998). These differences between SOCS-1 and SOCS-3 have been explained on the basis of a weaker affinity of SOCS-3 for JAK kinase (Masuhara et al., 1997; Sasaki et al., 1999). However, another possible explanation is that the primary binding target for SOCS-3 is not the JAK kinase, but other molecules within the signaling cascade such as the phosphorylated cytokine receptors or STAT proteins.

In work leading up to the present invention, the inventors sought to identify the molecular target of SOCS-3 and quantify the affinity of this interaction. Based on peptide binding data, the subject inventors have demonstrated that a single high affinity binding site exists for SOCS-3 on the gp130 receptor, centred around phosphotyrosine-757 (pY757). The letter "p" before a single letter abbreviation for an amino acid (e.g. "Y" for tyrosine) means the amino acid is phosphorylated. The numerical value after the amino acid letter is the residue number. Binding is phosphorylation dependent, and suppression of gp130 signaling by SOCS-3, but not SOCS-1, is impaired if this residue is mutated to phenylalanine. Furthermore, SOCS-3 binds to a gp130-derived pY757 phosphopeptide with an affinity that is approximately $10^4$-fold higher than binding to a phosphopeptide derived from the activation loop in JAK2, previously reported to be the biologically relevant docking site for SOCS-3 (Sasaki et al., 1999).

Taken together, these data show that suppression of gp130-mediated signaling by SOCS-3 involves recruitment to the phosphorylated receptor in a manner that is distinct to the mechanism of inhibition used by SOCS-1. These data also have similar implications in relation to other cytokine receptors such as erythropoietin (EPO) receptor and leptin receptor which have phosphotyrosine regions homologous to those recognized by SOCS-3 on gp130.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1, <400>2, etc. A sequence listing is provided after the claims.

One aspect of the present invention relates to a method for regulating signaling of a cytokine or related molecule in an animal subject, said method comprising administering to said animal or to a site within said animal an effective amount of a modulator of interaction between a SOCS molecule and a region within a cytoplasmic domain of a receptor for said cytokine or related molecule.

Another aspect of the present invention contemplates a method for regulating signaling of a cytokine or related molecule in an animal subject, said method comprising administering to said animal or to a site within said animal an effective amount of a modulator of interaction between a SOCS-3 or related molecule and a region within the cytoplasmic domain of a receptor for said cytokine or related molecule.

A further aspect of the present invention provides a method for regulating signaling of a cytokine or related molecule in an animal subject, said method comprising administering to said animal or to a site within said animal an effective amount of a modulator of interaction between a SOCS-3 or related molecule and a region within the cytoplasmic domain of a receptor for said cytokine or related molecule wherein said region comprises a phosphorylated tyrosine.

Still another aspect of the present invention contemplates a method for regulating signaling of a cytokine or related molecule in an animal subject, said method comprising administering to said animal or to a site within said animal an effective amount of a modulator of interaction between a SOCS-3 or related molecule and a region within the cytoplasmic domain of a receptor for said cytokine or related molecule wherein the receptor is selected from gp130, leptin receptor, EPO receptor or any other receptor having a region homologous to the amino acid sequence in the cytoplasmic domain of gp130 to which SOCS-3 binds.

Yet another aspect of the present invention contemplates a method of inhibiting signaling of a cytokine or related molecule in an animal subject, said method comprising administering to said animal or to a site within said animal an effective amount of an agonist of interaction between a SOCS molecule and a region within the cytoplasmic domain of a receptor for said cytokine or related molecule.

Still yet another aspect of the present invention provides a method of facilitating signaling of a cytokine or related molecule in an animal subject, said method comprising administering to said animal or to a site within said animal an effective amount of an antagonist of interaction between a SOCS molecule and a region within the cytoplasmic domain of a receptor for said cytokine or related molecule.

Even still another aspect of the present invention contemplates a method of identifying an agent capable of modulating signaling of a cytokine or related molecule, said method comprising screening for agents which are capable of interfering or otherwise antagonizing or promoting or otherwise agonizing interaction between a SOCS molecule and a cytoplasmic domain of a receptor for said cytokine or related molecule.

Even yet another aspect of the present invention contemplates a method for identifying a modulator of interaction between a. SOCS molecule or part, fragment, or derivative, or homologue or analogue thereof and a receptor for a cytokine or related molecule or part, fragment derivative or homologue or analogue thereof, said method comprising:— immobilizing one of said SOCS molecules or receptor or their parts, fragments, derivatives, homologues or analogues to a solid support via binding partners wherein one of said binding partners is attached or otherwise anchored to said solid support and another of said binding partners is linked to said SOCS or receptor molecules;

contacting said immobilized SOCS or receptor molecule with the other of receptor or SOCS molecule in the presence of a potential agonist or antagonist; and measuring qualitatively or quantitatively a change in signal emission indicative of enhanced or diminished binding between said SOCS and receptor or their parts, fragments, derivatives, homologues or analogues.

Another aspect of the present invention provides a method for identifying a modulator of interaction between a SOCS molecule or part, fragment, or derivative, or homologue or analogue thereof and a receptor for a cytokine or related molecule or part, fragment derivative or homologue or analogue thereof, said method comprising:— immobilizing said receptor or its parts, fragments, derivatives, homologues or analogues to a solid support via binding partners wherein one of said binding partners Is attached or otherwise anchored to said solid support and another of said binding partners is linked to said receptor molecule;

contacting said immobilized receptor molecule with said SOCS molecule or its parts, fragments, derivatives, homologues or analogues in the presence of a potential agonist or antagonist; and measuring qualitatively or quantitatively a change in signal emission indicative of enhanced or diminished binding between said SOCS and receptor or their parts, fragments, derivatives, homologues or analogues.

A further aspect of the present invention provides a method for identifying a modulator of interaction between a SOCS molecule or part, fragment, or derivative, or homologue or analogue thereof and a receptor for a cytokine or related molecule or part, fragment derivative or homologue or analogue thereof, said method comprising:— immobilizing one of said SOCS molecules or receptor or their parts, fragments, derivatives, homologues or analogues to a solid support via binding partners comprising biotin and streptavidin wherein one of said biotin or streptavidin is attached or otherwise anchored to said solid support and the another of said biotin or streptavidin is linked to said SOCS or receptor molecule;

contacting said immobilized SOCS or receptor molecule with the other of receptor or SOCS molecule in the presence of a potential agonist or antagonist; and measuring qualitatively or quantitatively a change in signal emission indicative of enhanced or diminished binding between said SOCS and receptor or their parts, fragments, derivatives, homologues or analogues.

Still another aspect of the present invention provides a method for identifying a modulator of interaction between a SOCS molecule or part, fragment, or derivative, or homologue or analogue thereof and a receptor for a cytokine or related molecule or part, fragment derivative or homologue or analogue thereof, said method comprising:— immobilizing said receptor or its parts, fragments, derivatives, homologues or analogues to a solid support via binding partners comprising biotin and streptavidin wherein streptavidin is attached or otherwise anchored to said solid support and said biotin is linked to said receptor molecule;

contacting said immobilized receptor molecule with said SOCS molecule or its parts, fragments, derivatives, homologues or analogues in the presence of a potential agonist or antagonist; and measuring qualitatively or quantitatively a change in signal emission indicative of enhanced or diminished binding between said SOCS and receptor or their parts, fragments, derivatives, homologues, or analogues.

Yet another aspect of the present invention contemplates a composition comprising a modulator of interaction between a SOCS molecule and a cytoplasmic domain of a receptor molecule, said composition further comprising one or more pharmaceutically acceptable carriers and/or diluents.

BRIEF DESCRIPTION OF THE FIGURES

FIG. 5 is a representation showing a comparison of murine and human gp130, human leptin and human EPO phosphopeptide binding sites.

DETAILED DESCRIPTION OF THE PREFERRED EMBODIMENTS

Figure 1A:
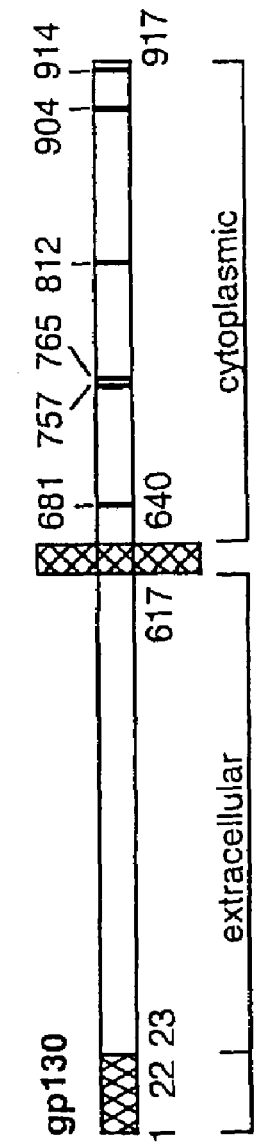
FIG. 1 is a photographic representation showing that gp130-derived phosphopeptide interacts specifically with SOCS-3. (A) Biotinylated phosphopeptides were synthesized corresponding to the regions of murine gp130 surrounding each cytoplasmic tyrosine residue (a pY812 peptide was not synthesized, as this tyrosine is not conserved in human gp130), or to regions surrounding the known tyrosine phosphorylation sites in STAT-1 and STAT-3. (B) Peptides shown in (A) were immobilized on streptavidin-agarose resin and incubated with recombinant SOCS-3. After washing and elution of bound protein, samples were analyzed by SDS-PAGE. Only the gp130 pY757 peptide showed any significant binding of SOCS-3 as detected by SDS-PAGE analysis of the resin eluates.

The present invention is predicated in part on the identification of the molecular target of a SOCS molecule. In particular, the molecular target is determined to be a region on the cytoplasmic domain of a receptor for the cytokine. The identification of this molecular target permits the development of assays to identify agonists and antagonists of cytokines or related molecule-mediated signal transduction. Such agonists and antagonists are useful in the manufacture of medicaments for the treatment of conditions involving aberrations in signal transduction.

Accordingly, one aspect of the present invention relates to a method for regulating signaling of a cytokine or related molecule in an animal subject, said method comprising administering to said animal or to a site within said animal an effective amount of a modulator of interaction between a SOCS molecule and a region within a cytoplasmic domain of a receptor for said cytokine or related molecule.

The present invention is particularly directed to the SOCS-3 molecule. This is done, however, with the understanding that the present invention extends to any SOCS molecule which regulates cytokine signaling via interaction with the cytoplasmic domain of a cytokine receptor. Most preferably, however, the SOCS molecule is SOCS-3.

Reference herein to a "SOCS-3" molecule includes all mutants and derivatives including parts and fragments thereof as well as homologues of SOCS-3. It also extends to analogues of SOCS-3 or analogues of parts or fragments of SOCS-3 which may be useful in assays for ligands. A "homologue" of SOCS-3 includes the equivalent or similar molecule from another species or a molecule which has similar physiological, biochemical, immunological or binding kinetic properties to SOCS-3. Identification of the species from which a particular SOCS-3 molecule is isolated is shown by the singles letters "h" for human and "m" for murine (e.g. mouse).

Reference herein to a "cytokine" is used in its broadest sense and includes molecules related to cytokines at the functional, biological, immunological or biochemical levels. A functionally related molecule may, for example, interact with the same receptor as a cytokine. Examples of related molecules include growth factors, growth hormones, leptin and chemokines.

In one particularly preferred embodiment, the cytokine receptor is gp130 or a functionally or structurally related receptor. However, the present invention extends to the cytoplasmic domain of any cytokine receptor or related molecule including the EPO receptor and the leptin receptor. Reference herein to a "receptor" includes both receptors specific for a particular cytokine as well as non-specific receptors capable of interaction with the cytokine or related molecule.

In an even more particularly preferred embodiment, the region on gp130 to which the SOCS-3 binds or otherwise interacts is a region spanning Y757 or other mammalian homologous regions in other receptors.

Accordingly, another aspect of the present invention contemplates a method for regulating signaling of a cytokine or related molecule in an animal subject, said method comprising administering to said animal or to a site within said animal an effective amount of a modulator of interaction between a SOCS-3 or related molecule and a region within the cytoplasmic domain of a receptor for said cytokine or related molecule.

Preferably the modulator inhibits SOCS-3 interaction with the cytoplasmic domain of a receptor.

Preferably the modulator inhibits SOCS-3 interaction with or proximal to a region comprising a phosphorylated tyrosine.

Accordingly, in a particularly preferred embodiment there is provided a method for regulating signaling of a cytokine or related molecule in an animal subject said method comprising administering to said animal or to a site within said animal an effective amount of a modulator of interaction between a SOCS-3 or related molecule and a region within the cytoplasmic domain of a receptor for said cytokine or related molecule wherein said region comprises a phosphorylated tyrosine.

In a particularly preferred embodiment, the phosphorylated tyrosine (Y) is at position 757 (i.e. pY757) or its functional equivalent in other receptors.

Examples of regions within particular receptors comprising a tyrosine which is capable of phosphorylation and which is proximal to where SOCS-3 or a related molecule binds include the following:—

```
mgp 130          Y757 STASTVEYSTVVHSG  [SEQ ID NO:4]
hgp 130          Y757 NTSSTVQYSTVVHSG  [SEQ ID NO:5]
leptin receptor  Y985 QRQPFVKYATLISNS  [SEQ ID NO:6]
EPO receptor     Y401 ASAASFEYTILDPSS. [SEQ ID NO:7]
```

The terms "Y757", "Y985" and "Y401" relate to the residue number of the phosphorylated tyrosine residue.

Accordingly, another aspect of the present invention contemplates a method for regulating signaling of a cytokine or related molecule in an animal subject, said method comprising administering to said animal or to a site within said animal an effective amount of a modulator of interaction between a SOCS-3 or related molecule and a region within the cytoplasmic domain of a receptor for said cytokine or related molecule wherein the receptor is selected from gp130, leptin receptor, EPO receptor or any other receptor having a region homologous to the amino acid sequence in the cytoplasmic domain of gp130 to which SOCS-3 binds.

Examples of other receptors having homologous regions to those in gp130 which interact with SOCS-3 include the IL-6 family of receptors such as those which interact with leukemia inhibitory factor (LIF), CNTF, interleukins such as IL-6 and IL-11, OSM and cardiotrophin-1 (CT-1).

Reference to these specific receptors and target amino acid sequences includes reference to mutants and derivatives including fragments and parts thereof as well as homologues and analogues thereof.

The preferred animal subject of the present invention is a human, however, the present invention extends to primates, livestock animals (e.g. sheep, pigs, cows, goats, horses), laboratory test animals (e.g. mice, rats, guinea pigs, hamsters), companion animals (e.g. dogs, cats) or captive wild animals.

The modulator of interaction between a SOCS molecule (e.g. SOCS-3) and a receptor may be an agonist or antagonist. In essence, a molecule which promotes or otherwise facilitates SOCS binding is an agonist of SOCS but such a molecule acts to inhibit cytokine- or related molecule-mediated signal transduction. Conversely, an antagonist of SOCS interaction facilitates cytokine- or related molecule-mediated signal transduction.

Accordingly, another aspect of the present invention contemplates a method of inhibiting signaling of a cytokine or related molecule in an animal subject, said method comprising administering to said animal or to a site within said animal an effective amount of an agonist of interaction between a SOCS molecule and a region within the cytoplasmic domain of a receptor for said cytokine or related molecule.

In an alternative embodiment, the present invention provides a method of facilitating signaling of a cytokine or related molecule in an animal subject, said method comprising administering to said animal or to a site within said animal an effective amount of an antagonist of interaction between a SOCS molecule and a region within the cytoplasmic domain of a receptor for said cytokine or related molecule.

Preferably, the SOCS molecule is SOCS-3 or a related molecule. More preferably, the SOCS molecule is SOCS-3.

Preferably, the site of interaction between the SOCS molecule and the receptor comprises or is proximal to a site comprising a phosphorylated tyrosine. In a particular preferred embodiment, the receptor and site of interaction is selected from:—

| | | |
|---|---|---|
| mgp 130 | Y757 | STASTVEYSTVVHSG [SEQ ID NO:4] |
| hgp 130 | Y757 | NTSSTVQYSTVVHSG [SEQ ID NO:5] |
| leptin receptor | Y985 | QRQPFVKYATLISNS [SEQ ID NO:6] |
| EPO receptor | Y401 | ASAASFEYTILDPSS, [SEQ ID NO:7] | or their mammalian equivalents or homologues thereof or their mutants and derivatives including parts and fragments thereof.

Reference to equivalents, homologues, mutants and derivatives including parts and fragments thereof preferably includes regions carrying the SH2 domain. The present invention is particularly directed to the use of a phosphopeptide comprising an SH2 domain or equivalent region in the detection of antagonists and agonists in the interaction between this region and the cytoplasmic domain of a cytokine or related molecule receptor.

The agent capable of agonizing or antagonizing interaction between the SOCS molecule and the cytoplasmic domain of the cytokine receptor may be a proteinaceous or non-proteinaceous molecule. A proteinaceous molecule includes a peptide, polypeptide or protein or a complex thereof with, for example, a lipid, phospholipid or carbohydrate. A proteinaceous molecule may also be modified by the attachment of one or more non-proteinaceous sections or portions A non-proteinaceous molecule includes any organic chemical. Conveniently, the agent is identified following screening of a chemical library. Chemical libraries are well known to those skilled in the art and may be derived from natural product sources such as but not limited to coral, plants and plant parts including bark, roots, flowers, leaves and stems, micro-organisms, marine macro-organisms and insects. Alternatively, chemical libraries may be collections of synthetic organic compounds or be produced by combinatorial chemical approaches. Alternatively, non-proteinaceous molecules may be produced through rational design, or through other conventional chemical approaches. A non-proteinaceous molecule may also be modified by the attachment of one or more proteinaceous sections or portions.

Any number of screening procedures may be adopted to identify the agonists and antagonist. In one example, a cytokine receptor is linked to a reporter molecule such that upon interaction between a SOCS molecule and the receptor, the reporter molecule provides an identifiable signal. An "identifiable signal" may be presence of a signal or absence of a signal. The amount or extent of signaling is then measured, quantitatively or qualitatively in the presence of potential agonists or antagonists. Any number of variations may be adopted to screen for agonists and antagonists. Variations of two hybrid screening and phage labelling may also be employed. Cell based assays and molecular assays may also be employed.

Accordingly, another aspect of the present invention contemplates a method of identifying an agent capable of modulating signaling of a cytokine or related molecule, said method comprising screening for agents which are capable of interfering or otherwise antagonizing or promoting or otherwise agonizing interaction between a SOCS molecule and a cytoplasmic domain of a receptor for said cytokine or related molecule.

The SOCS molecule and/or receptor molecule may be parts, fragments, derivatives, homologues or chemical analogues of all or a portion of the molecule. A portion of SOCS could include the SH2 domain or its equivalent.

More particularly, and in one preferred method, agonists and antagonists of SOCS interaction with a receptor are identified using biosensor technology. In one embodiment, phosphopeptides derived from a receptor or its mutants, derivatives, homologues or analogues are biotinylated such as in or at their N-terminal region. The biotinylated phosphopeptides are then immobilized to a solid support such as the surface of a chip via a streptavidin coating. A SOCS molecule capable of interacting with all and some of the immobilized phosphopeptides or binding portions or fragments or derivatives or homologues or analogues of a SOCS molecule are then brought into contact with immobilized phosphopeptides. Such interactions may be in the presence or absence or a range of potential agonists or antagonists. Sensorgrams are then compiled to identify or analyse binding signals such as electrical or optical signals. Biotin/streptavidin represents one convenient means of immobilizing binding peptide. However, any of a host of other capturing pairs or binding partners may be used provided that these do not interfere with binding of the SOCS molecule or agonist/antagonist.

Accordingly, another aspect of the present invention contemplates a method for identifying a modulator of interaction between a SOCS molecule or part, fragment, or derivative, or homologue or analogue thereof and a receptor for a cytokine or related molecule or part, fragment derivative or homologue or analogue thereof, said method comprising:— immobilizing one of said SOCS molecules or receptor or their parts, fragments, derivatives, homologues or analogues to a solid support optionally via binding partners wherein one of said binding partners is attached or otherwise anchored to said solid support and another of said binding partners is linked to said SOCS or receptor molecules;

contacting said immobilized SOCS or receptor molecule with the other of receptor or SOCS molecule in the presence of a potential agonist or antagonist; and measuring qualitatively or quantitatively a change in signal emission indicative of enhanced or diminished binding between said SOCS and receptor or their parts, fragments, derivatives, homologues or analogues.

Preferably, the SOCS molecules in SOCS-3 or a related molecule. Most preferably, the SOCS molecule in SOCS-3. Although the SOCS molecule or receptor may be first immobilized to the solid support, it is particularly convenient for the receptor or a part, fragment, derivative, homologue or analogue to be anchored. Preferably, anchoring is via binding partners although the present invention extends to direct binding of the SOCS molecule or receptor molecule or portions thereof to the solid support.

According to these preferred embodiments, there is provided a method for identifying a modulator of interaction between a SOCS molecule or part, fragment, or derivative, or homologue or analogue thereof and a receptor for a cytokine or related molecule or part, fragment derivative or homologue or analogue thereof, said method comprising:— immobilizing said receptor or its parts, fragments, derivatives, homologues or analogues to a solid support optionally via binding partners wherein one of said binding partners is attached or otherwise anchored to said solid support and another of said binding partners is linked to said receptor molecule;

contacting said immobilized receptor molecule with said SOCS molecule or its parts, fragments, derivatives, homologues or analogues in the presence of a potential agonist or antagonist; and measuring qualitatively or quantitatively a change in signal emission indicative of enhanced or diminished binding between said SOCS and receptor or their parts, fragments, derivatives, homologues or analogues.

The solid support is preferably in the form of a chip such as a biochip.

Any anchoring means may be employed to anchor the molecules to the solid support. Generally, binding pairs are employed such as but not limited to biotin/streptavidin, DNA/DNA binding protein, antibody/antigen, FLAG/anti-FLAG antibodies, protein/protein binding molecule and complementary nucleic acid molecules.

The signal emission may be in any convenient means. Generally, interaction or loss of interaction between a SOCS molecule and a receptor or fragments, parts, derivatives, homologues or analogues thereof causes or otherwise facilitates production of an electrical or optical signal via a suitable biological recognition system and electrochemical transducer. Electrochemical transducers include potentiometric, amperometric, optical and other physicochemical transducers. Potentiometric devices measure the accumulation of charge density at the surface of an electrode; amperometric sensors monitor currents generated when electrons are exchanged between a biological system and an electrode; an optical biosensor correlates changes in concentration, mass, or number to direct changes in the characteristics of light; other physicochemical sensors monitor biological interactions through changes in enthalpy, ionic conductance and mass. An "electrode" may also include a chip such as a biochip.

The streptavidin coated biosensor chips from pharmacia are particularly useful in the practice of the present invention.

According to this preferred embodiment there is provided a method for identifying a modulator of interaction between a SOCS molecule or part, fragment, or derivative, or homologue or analogue thereof and a receptor for a cytokine or related molecule or part, fragment derivative or homologue or analogue thereof, said method comprising:— immobilizing one of said SOCS molecules or receptor or their parts, fragments, derivatives, homologues or analogues to a solid support optionally via binding partners comprising biotin and streptavidin wherein one of said biotin or streptavidin is attached or otherwise anchored to said solid support and the another of said biotin or streptavidin is linked to said SOCS or receptor molecule;

contacting said immobilized SOCS or receptor molecule with the other of receptor or SOCS molecule in the presence of a potential agonist or antagonist; and measuring qualitatively or quantitatively a change in signal emission indicative of enhanced or diminished binding between said SOCS and receptor or their parts, fragments, derivatives, homologues or analogues.

In a preferred embodiment, anchoring of the receptor to the solid support is via biotin and streptavidin.

More particularly, there is provided a method for identifying a modulator of interaction between a SOCS molecule or part, fragment, or derivative, or homologue or analogue thereof and a receptor for a cytokine or related molecule or part, fragment derivative or homologue or analogue thereof, said method comprising:— immobilizing said receptor or its parts, fragments, derivatives, homologues or analogues to a solid support optionally via binding partners comprising biotin and streptavidin wherein streptavidin is attached or otherwise anchored to said solid support and said biotin is linked to said receptor molecule;

contacting said immobilized receptor molecule with said SOCS molecule or its parts, fragments, derivatives, homologues or analogues in the presence of a potential agonist or antagonist; and measuring qualitatively or quantitatively a change in signal emission indicative of enhanced or diminished binding between said SOCS and receptor or their parts, fragments, derivatives, homologues or analogues.

Another useful biosensor employs Surface Plasmon Resonance (SPR) developed by Quantech Ltd. SPR is a quantum optical-electrical assay and is based on coupling or transferring energy carried by photons of light to electrons in a metal. The wavelength of light at which coupling (i.e. energy transfer) occurs is characteristic of the particular metal and the environment of the metal surface which is illuminated. When there is a match or resonance between the energy of the light photons and the electrons at the metal surface, a transfer of energy occurs. The coupling, can be observed by measuring the amount of light reflected by the metal surface. All the light at most wavelengths is reflected except at the resonant wavelength, where almost all the light is absorbed. The measuring device is, in effect a reflectance spectrophotometer.

The coupling of light into a metal surface results in the creation of a plasmon, a group of excited electrons which behave like a single electrical entity. The plasmon, in turn, generates an electrical field which extends about 100 nanometers above and below the metal surface. The characteristic of this phenomenon which makes SPR an analytical tool is that any change in the chemical composition of the environment within the range of the plasmon field causes a change in the wavelength of light which is absorbed rather than reflected and the magnitude of the shift is quantitatively related to the magnitude of the chemical change.

There are many other protocols for identifying binding or absence of binding or a reduction and these are encompassed by the present invention. Other such protocols include electrophoretic and chromatographic detection means.

As described above, chemical analogues of a SOCS molecule and/or a receptor are usefully employed in screening assays for ligands (e.g. agonists or antagonists) due to enhanced chemical stability and/or coupling and/or signaling due to the chemical modifications. All such chemical modification to the SOCS molecules or receptor molecules including to their parts, fragments, portions, derivatives or homologue are contemplated by the present invention. Reference herein to a "SOCS" molecule or a "receptor" molecule includes analogues and in particular chemical analogues including chemical modifications. Chemical modifications include modifications to side chains of peptides, polypeptides and proteins.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methyl-butyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-Nmethylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-τ-butylglycine | Nmtbug |

TABLE 1-continued

| Non-conventional amino acid | Code | Non-conventional amino acid | Code |
|---|---|---|---|
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-τ-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-τ-butylglycine | Mtbug |
| L-α-methylcysteine | Mcys | L-methylethylglycine | Metg |
| L-α-methylglutamine | Mgln | L-α-methylglutamate | Mglu |

TABLE 1-continued

| Non-conventional amino acid | Code | Non-conventional amino acid | Code |
|---|---|---|---|
| L-α-methylhistidine | Mhis | L-α-methylhomophenyl-alanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenyl-alanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenyl-alanine | Nmhphe |
| N-(N-(2,2-diphenyl-ethyl) carbamyl-methyl)glycine | Nnbhm | N-(N-(3,3-diphenylpropyl) carbamylmethyl)glycine | Nnbhe |
| 1-carboxy-1-(2,2-diphenyl-ethylamino)cyclo-propane | Nmbc | | |

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

Still a further aspect of the present invention is directed to an agent useful for modulating signaling of a cytokine or a related molecule, said agent capable of interfering or otherwise antagonizing or promoting or otherwise agonizing interaction between a SOCS molecule and a cytoplasmic domain of a receptor for said cytokine or related molecule.

Preferably, the SOCS molecule is SOCS-3 or related molecule. Most preferably, the SOCS molecule is SOCS-3. The preferred receptors comprise a phosphorylated tyrosine in a region comprising or proximal to the site of interaction with the SOCS molecule.

The present invention, therefore, contemplates a composition comprising a modulator of interaction between a SOCS molecule and a cytoplasmic domain of a receptor molecule, said composition further comprising one or more pharmaceutically acceptable carriers and/or diluents.

The modulator may be an agonist or an antagonist of the SOCS/receptor interaction and may be useful in modulating cytokine- or related molecule-mediated signal transduction. This may be useful in a range of conditions including cancer, inflammatory disorders and autoimmune and other immunological disorders. The composition may be regarded as a pharmaceutical composition and/or an agent.

Composition forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

When the modulator is suitably protected, it may be orally administered, for example, with an inert diluent or with an assimilable edible carrier, or it may be enclosed in hard or soft shell gelatin capsule, or it may be compressed into tablets, or it may be incorporated directly with the food of the diet or administered via breast milk. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of modulator. The percentage of the compositions and preparations may, of course, be varied and may conveniently be between about 5 to about 80% of the weight of the unit. The amount of modulator in such therapeutically useful compositions is such that a suitable dosage will be obtained. Preferred compositions or preparations according to the present invention are prepared so that an oral dosage unit form contains between about 0.1 µg and 200 mg of modulator. Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules, creams and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, anti-bacterial and anti-fungal agents, isotonic and absorption delaying agents and the like. The use of such media and agents for pharmaceutical active substances is well known in the art and except insofar as any conventional media or agent is incompatible with the modulator, their use in the therapeutic compositions is contemplated. Supplementary active compounds can also be incorporated into the compositions.

The composition may also comprise genetic molecules such as a vector capable of transfecting target cells where the vector carries a nucleic acid molecule capable of encoding a modulator, when the modulator is a proteinaceous molecule. The vector may, for example, be a viral vector. In this regard, a range of gene therapies are contemplated by the present invention including isolating certain cells, genetically manipulating and returning the cell to the same subject or to a genetically related or similar subject.

The present invention further contemplates antibodies and other immunological reagents directed to the modulators identified by the subject screening assays.

The present invention is further directed to a use of a SOCS molecule and/or its receptor in the manufacture of an assay to screen for agonists or antagonists of SOCS/receptor interaction.

The present invention is further described by the following non-limiting Examples.

EXAMPLE 1

SOCS-3 Protein Expression

Murine SOCS-3 cDNA was PCR-amplified and cloned into the NdeI/BamHI sites of pET15b (Novagen). The hexahistidine tagged protein was expressed in BL21 DE3 pLysS *E. coli* (Stratagene) and purified from cells lysed with 7 M guanidinium hydrochloride by immobilized metal affinity chromatography. Purified protein was refolded by dialysis into PBS containing 2 mM DTT, 2 mM EDTA and 0.02% v/v Tween 20. Refolded material was purified to homogeneity by ion exchange chromatography on a Mono S column (Pharmacia). Recombinant SOCS-3 was characterized by SDS-PAGE analysis, and MALDI mass spectrometry. The concentration of a stock solution of SOCS-3 used for quantitative binding analyses was determined by amino acid analysis.

EXAMPLE 2

Peptide Synthesis

All synthetic peptides were synthesized with C-terminal amides using a Rink amide MBHA resin support and Fmoc amino acids activated with HBTU. Phosphotyrosine-containing peptides were prepared using Fmoc-O-benzyl-L-phosphotyrosine which was activated with HATU, and coupled for 1 hour. Deprotection and cleavage was effected using 95% trifluoroacetic acid containing 5% triisopropylsilane, and crude peptides were purified by reverse phase HPLC. Purified peptides were characterized by MALDI mass spectrometry. Biotinylated peptides were prepared by coupling α-biotin to the amino terminus of resin-bound peptides prior to cleavage and deprotection.

EXAMPLE 3

Qualitative Analysis of SOCS-3 Phosphopeptide Interactions

Biotinylated phosphopeptides were prepared corresponding to fragments of murine gp130 surrounding each cytoplasmic tyrosine residue (FIG. 1A), with the exception of tyrosine 859 which is not conserved in the human receptor. Biotinylated phosphopeptides were also prepared corresponding to the known tyrosine phosphorylation sites in murine STAT-1 (Y701) and STAT-3 (Y705). Biotinylated peptides were immobilized onto streptavidin-agarose resin (Pierce), and 20 μL of these resins were incubated for 1 hour at room temperature with 1 mL of 50 μg/mL SOCS-3 in 10 mM Tris pH 7.5 containing 0.1% v/v Tween-20. Following removal of the protein solution, resin was washed twice with 1 mL PBS/0.1% v/v Tween-20, and bound protein eluted with 25 μL of SDS sample buffer containing 10 mM DTT, Samples were analyzed by SDS-PAGE on 12% w/v polyacrylamide gels.

EXAMPLE 4

Biosensor Analyses

Phosphopeptides containing an N-terminal biotin moiety were immobilized onto a streptavidin-coated Biosensor chip (Pharmacia) at a density of ~200 Resonance Units (Rus). Binding of recombinant SOCS-3 was measured by flowing solutions of protein diluted into PBS, 0.1% v/v Tween 20 over the chip at a flow rate of 15 μL/min. For kinetic analysis of SOCS-3 binding, samples of protein were diluted and immediately analysed to minimize losses of protein due to surface absorption. Following each binding measurement, residual SOCS-3 was stripped from the immobilized ligand by washing with 6 M guanidinium hydrochloride (pH 8.0), followed by PBS, 0.1% v/v Tween 20. Binding profiles were analyzed using the BIAevaluation software version 3.0 (Pharmacia). To correct for non-specific binding, sensorgrams obtained for binding of SOCS-3 to the non-cognate gp130(674-688) phosphopeptide were subtracted from those for binding to the gp130(750-764) phosphopeptide. The dissociation constant $K_d$ was calculated from a Scatchard type analysis of the equilibrium response measurements obtained at different concentrations of SOCS-3.

A competitive binding assay for measuring the affinities of SOCS-3 ligands in solution was developed using the Biosensor instrument. Briefly, the phosphorylated gp130 (750-764) peptide, containing an N-terminal biotin moiety, was immobilized onto a streptavidin Biosensor chip. A dilution series of peptide, ligand was incubated with a fixed subsaturating amount of SOCS-3 (~100 nM) in a PBS, 0.1% v/v Tween 20 buffer containing 0.5 mg/mL BSA. Samples were left overnight at 4° C. prior to analysis on the Biosensor so that the rate of protein loss due to absorption was minimal through the course of the experiment. The response level of bound protein was recorded at a fixed time point within the sensorgram, and divided by the corresponding level of SOCS-3 bound to the peptide-chip in the absence of competing ligand. These fractional binding values (f) were fitted to the equation $f=1/(1+(c/IC_{50})^m)$ where c=the concentration of soluble SOCS-3 ligand, m=the curvature constant and $IC_{50}$ values correspond to the concentration of ligand required to displace 50% of the bound SOCS-3.

EXAMPLE 5

Luciferase Assays, Immunoprecipitation and Western Analysis

Generation of the expression vectors for SOCS-1 and SOCS-3, luciferase assays and Western blot analysis have been described previously (Nicholson et al., 1999). Briefly, 293T cells were transiently transfected with SOCS expression plasmids, a LIF-responsive reporter construct (APRE-luc; Endo et al., 1997) and a β-galactosidase reporter construct under a constitutive promoter (Srα-β-gal; Ogilvy et al., 1998). Luciferase activity from triplicate samples was determined and normalized against β-galactosidase activity.

EXAMPLE 6

Identification of pY757 in gp130 as a Potential SOCS-3 Interaction Site

Figure 1B:
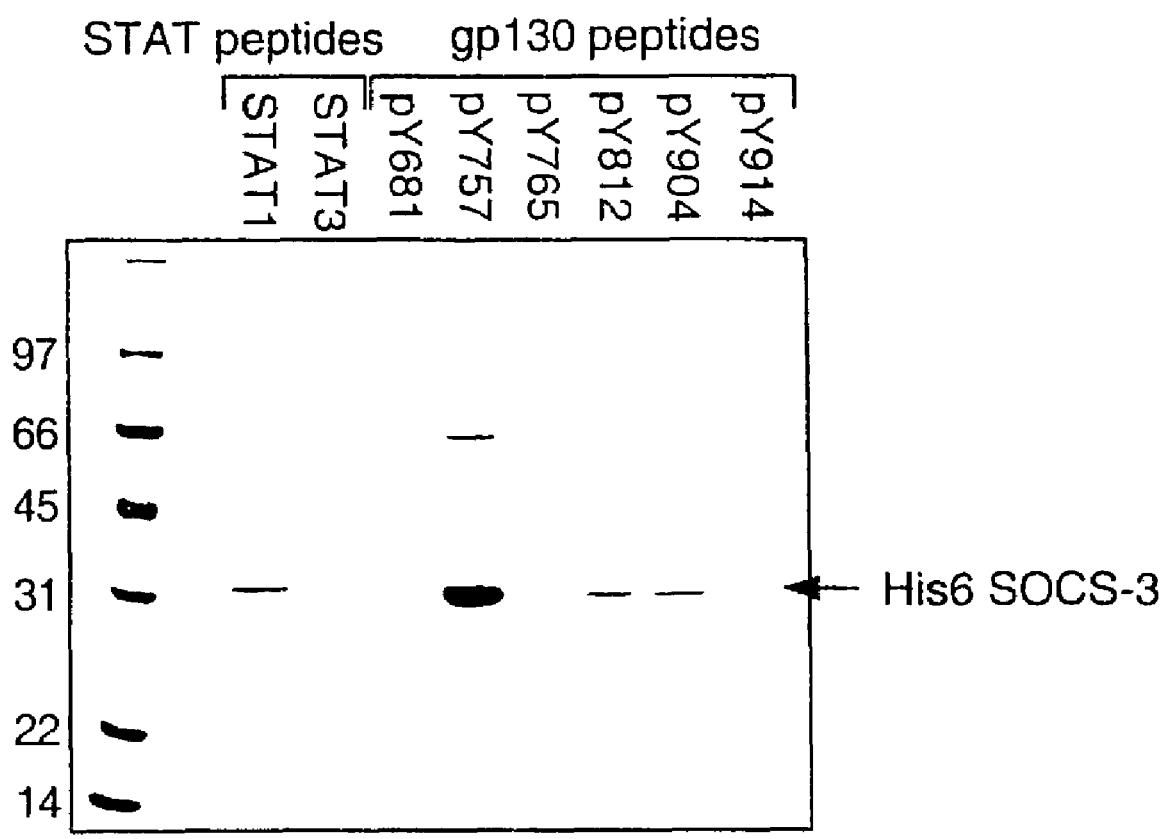

SOCS-3 expression (like that of SOCS-1) is induced by the IL-6 family of cytokines and can inhibit their biological actions (Masuhara et al., 1997; Minamoto et al., 1997; Nicholson et al., 1999; Starr et al., 1997). These cytokines utilize common features of the JAK-STAT signaling pathway—each shares gp130 as a common co-receptor, while JAKs 1, 2 and STAT-1 and -3 are responsible for transmitting the downstream signals. Thus a common mechanism of inhibition for each of the IL-6 family cytokines might require that SOCS-3 interact with either gp130, the JAK kinases, or STAT proteins. Association between SOCS-3 and the JH1 (kinase) domain of JAK2 has been previously demonstrated in qualitative "pull-down" experiments, moreover, the site of interaction has been identified as the autophosphorylation site within the activation loop (Sasaki et al., 1999). To investigate whether SOCS-3 might interact with tyrosine phosphorylated sites within gp130 or relevant STAT proteins, the inventors prepared phosphopeptides corresponding to regions surrounding each of the gp130 cytoplasmic tyrosine residues, in addition to peptides based on the known tyrosine phosphorylation sites within STAT-1 and STAT-3 (FIG. 1A). These peptides contained an N-terminal biotin moiety and were immobilized onto streptavidin-agarose resin. Recombinant SOCS-3 was incubated with peptide resin, and after washing, any bound protein was eluted with SDS sample buffer. SDS-PAGE analysis showed that only one peptide was able to efficiently capture SOCS-3 (FIG. 1B). This peptide represented a fragment of gp130 corresponding to amino acids 750-764 and was centred around the phosphorylated tyrosine residue 757 (pY757).

EXAMPLE 7 gp130 Contains a High Affinity, Phosphorylation-Dependent SOCS-3 Binding Site Centred Around pY757

Figure 2A:
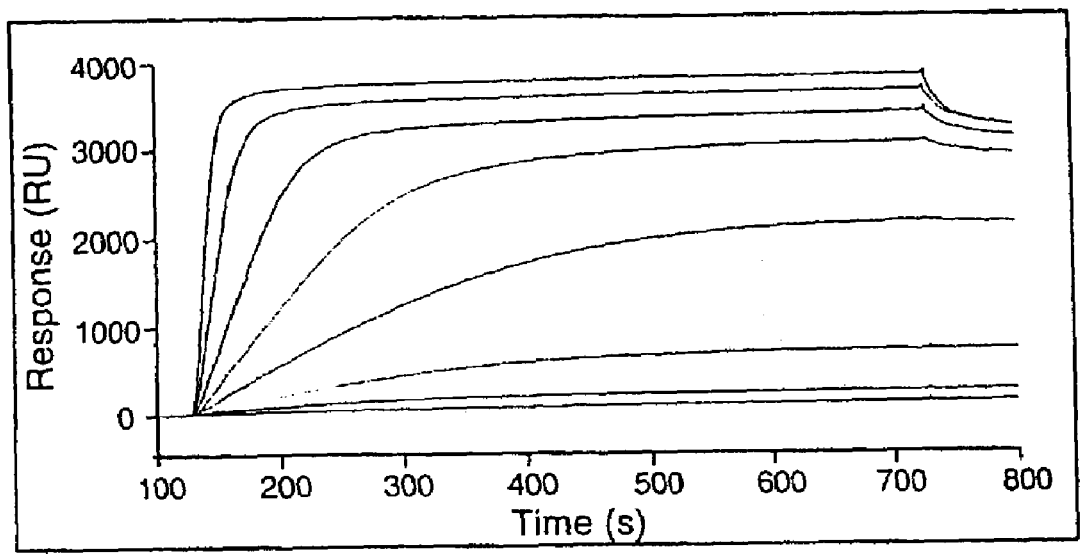
FIG. 2 is a graphical representation showing functional characterization of SOCS-3 protein. (A) Biosensor analysis of SOCS-3 binding to the gp130-derived phosphopeptide biotin-STASTVEpYSTVVHSG. [SEQ ID NO:4] Sensorgrams correspond to a 2-fold serial dilution series of SOCS-3 (8.65-1110 nM) passed over a chip bearing the immobilized peptide. (B) Determination of binding constants by Scatchard-type analysis. Data shown in (A) was used to calculate the association constant for SOCS-3 binding to the immobilized gp130 peptide. Plateau response values at equilibrium (RU) for the four highest concentrations of SOCS-3 used were plotted against the ratio of response to SOCS-3 concentration (RU/c). The association binding constant ($K_A$=2.38×10$^7$ M$^{-1}$) was calculated from the slope of the plot of RU/c versus RU. The dissociation constant=1$K_A$=42 nM.
Figure 2B:
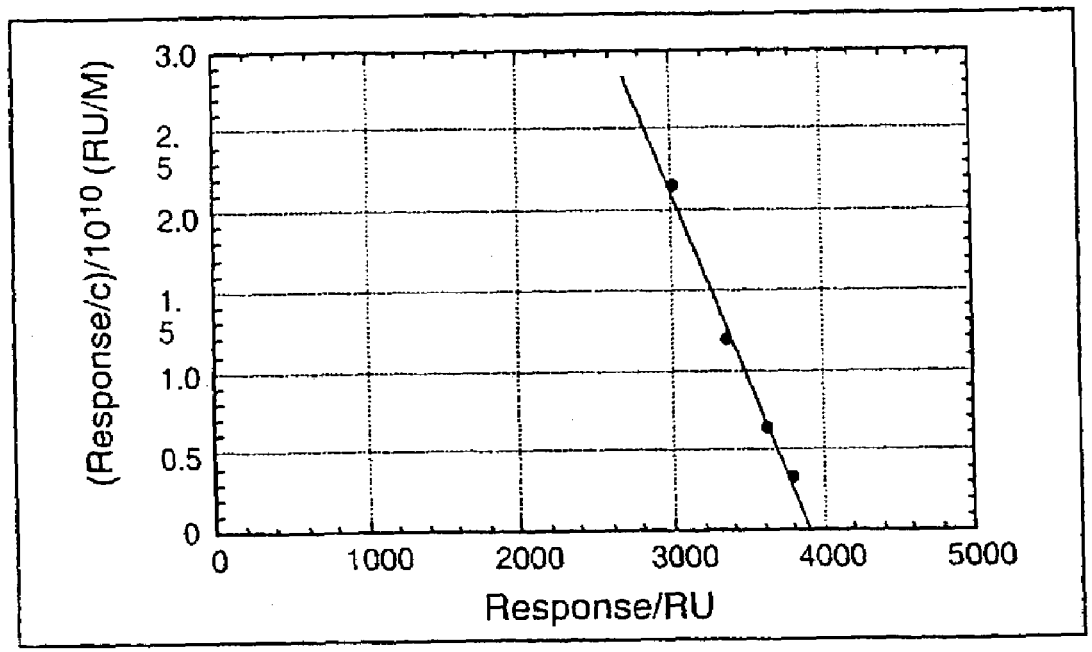

The binding affinity of SOCS-3 to the phosphorylated gp130(750-764) peptide was measured using surface plasmon resonance (SPR). The biotinylated form of this peptide was immobilized onto a streptavidin biosensor chip and binding of recombinant SOCS-3 was analyzed by SPR on a Biosensor instrument. As a non-specific control, the phosphorylated gp130(674-688) peptide was also immobilized in a separate channel on the same chip. Concentration-dependent binding of SOCS-3 to the immobilized gp130 (750-764) phosphopeptide was observed (FIG. 2A), while no specific binding was detected to the gp30(674-688) phosphopeptide. The dissociation constant for peptide binding was calculated from a Scatchard analysis of the equilibrium response values at different concentrations of SOCS-3 (FIG. 2B). The affinity of this interaction ($K_d$=42 nM) is high relative to that for the other peptides and characteristic of the binding constants observed for other SH2 domains binding to high affinity phosphopeptide ligands.

Figure 3A:
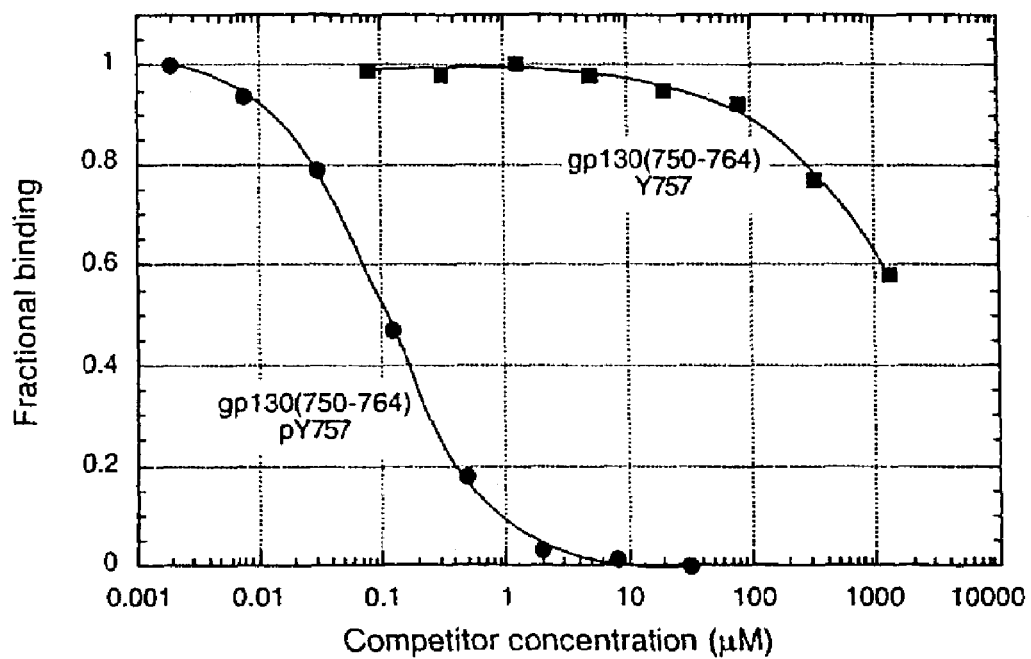
FIG. 3 is a graphical representation showing a comparison of SOCS-3 affinity for phosphorylated versus non-phosphorylated gp130 peptide, and JAK-derived peptides. (A) Solution binding of phosphorylated and non-phosphorylated forms of gp130 (750-764) peptide to SOCS-3 was measured in a competitive binding assay. The IC50's for inhibition of SOCS-3 binding to immobilized ligand were 110±4.6 nM for the phosphorylated peptide and 2.1±0.2 mM for the unphosphorylated peptide. (B) Solution binding of JAK-derived peptides to SOCS-3 measured in the competitive binding assay. These phosphopeptides represent the activation loop sequences in JAK1, 2 and 3 and contain a phosphotyrosine residue corresponding to the autophosphorylation site. The amino acid sequences of these peptides were JAK1: IETDKE(pY)YTVKDDRD (SEQ ID NO:1), JAK2: LPQDKE(pY)YKVKEPGE (SEQ ID NO:2), JAK3: LPLGKD(PY)YVVREPGQ (SEQ ID NO:3). The IC50 values for these peptides were: JAK1, 230±6.6 mM; JAK2, 1200±50 mM; JAK3, 140±4.8 mM. The IC50 value for the gp130 (750-764) phosphopeptide, run in the same experiment, was 110±4.6 nM.

To ascertain whether SOCS-3 binding was dependent upon the phosphorylation state of the peptide, a competitive binding assay was developed using the Biosensor instrument (Karlsonn, 1994). A subsaturating amount of SOCS-3 was incubated with different dilutions of a soluble competing peptide, and this mixture was then passed over the biosensor chip containing the immobilized gp130(750-764) phosphopeptide. $IC_{50}$ values were determined from plots of soluble peptide concentration versus fractional SOCS-3 bound. By this method, the relative binding affinities for phosphorylated and non-phosphorylated gp130(750-764) peptides were determined (FIG. 3A). While an $IC_{50}$ value of 110 nM was obtained for the phosphorylated peptide, the non-phosphorylated analogue bound with an $IC_{50}$ of 2.0 mM. Thus, binding of SOCS-3 to the gp130(750-764) peptide is phosphorylation-dependent, with an 18,000-fold difference in affinity mediated by the phosphate moiety. The inventors also used this competition assay to reassess the potential solution binding of the phosphopeptides listed in FIG. 1A. With the exception of the biotinylated gp130(750-764) phosphopeptide, none of these peptides showed measurable binding to SOCS-3 at concentrations up to 100 μM.

EXAMPLE 8

SOCS-3 Binds Selectively to gp130, But Only Weakly to JAK Kinase Peptides

Figure 3B:
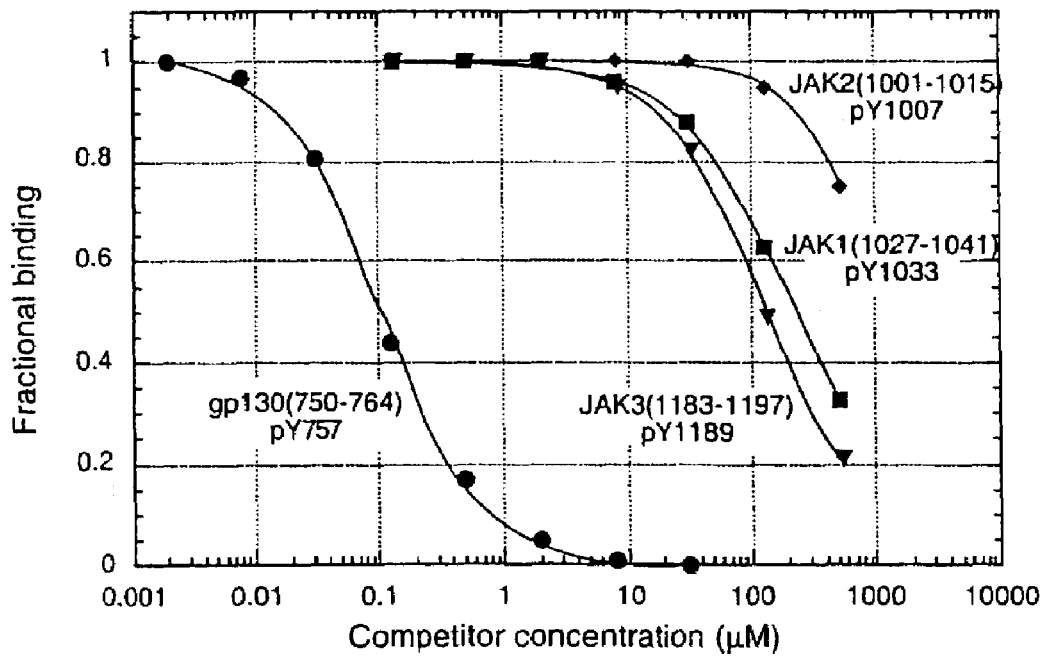
Figure 4A:
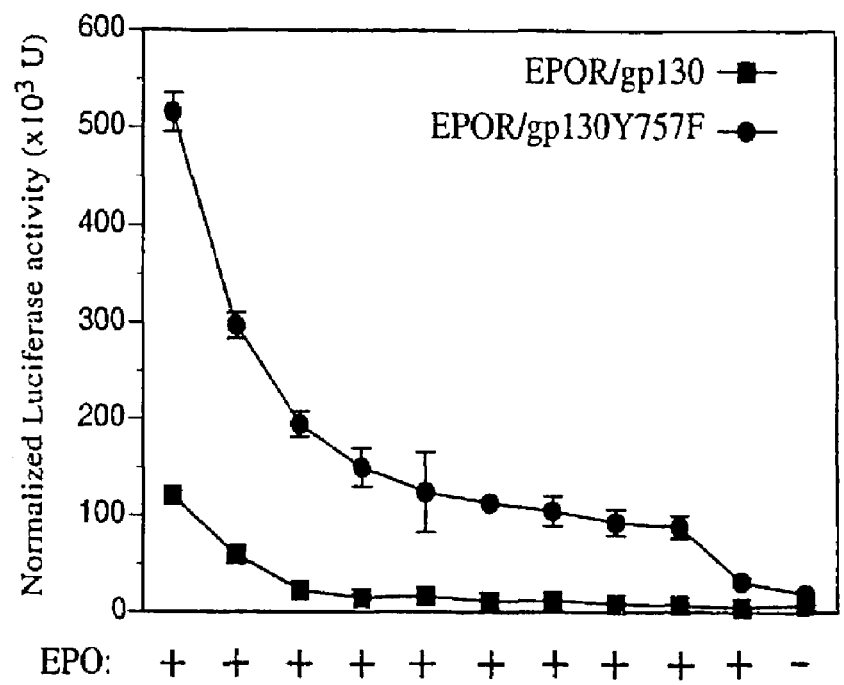
FIG. 4 is a photographic representation showing that SOCS-3, but not SOCS-1, inhibition of gp130 signaling is mediated through gp130 tyrosine 757. (A) 293T cells were transiently transfected with cDNAs expressing SOCS-1 and either EPO/gp130 or EPO/gp130Y757F in the presence of the APRE-luc and Srα-β-gal reporter genes. Cells were incubated in the presence (+) or absence (−) of 10 U/ml hEPO overnight and cell extracts prepared. Luciferase activity from triplicate samples was determined and normalized against β-galactosidase activity. (B) SOCS-1 protein levels in 293T cells expressing EPO/gp130 were determined by Western blot with anti-Flag antibody. (C) SOCS-1 protein levels in 293T cells expressing EPO/gp130Y757F. (D) 293T cells were transiently transfected with cDNAs expressing SOCS-3 and either EPO/gp130 or EPO/gp130Y757F in the presence of the APRE-luc and Srα-β-gal reporter genes. (E) SOCS-3 protein levels in 293T cells expressing EPO/gp130 were determined by Western blot with anti-Flag antibody. (F) SOCS-3 protein levels in 293T cells expressing EPO/gp130Y757F.
Figure 4B:
Figure 4C:
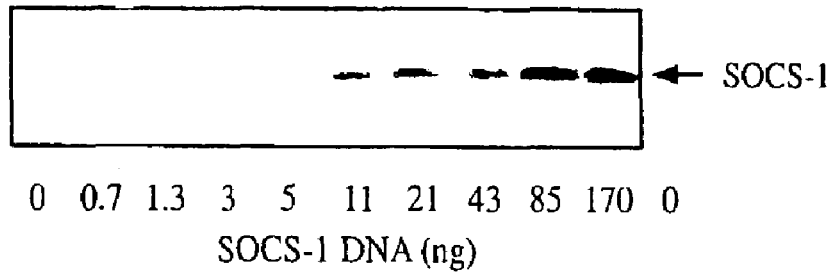

Earlier reports (Sasaki et al., 1999) have demonstrated that endogenous SOCS-3 is able to associate with full length JAK2. This interaction was mapped to the JH1 (kinase) domain of JAK2, and preparation and assaying of a series of phosphopeptides corresponding to known tyrosine phosphorylation sites within this domain identified residue pY1007 as the site of SOCS-3 interaction. This corresponds to the activation loop within the kinase domain of JAK2. The inventors, therefore, sought to make a quantitative comparison between the affinity of SOCS-3 for the gp130 (750-764) phosphopeptide versus phosphopeptides derived from the activation loops of JAKs 1-3. The affinities of the JAK-derived phosphopeptides for SOCS-3 were measured in the competitive binding assay, and the binding constants were compared to that for the gp130 (750-764) phosphopeptide (FIG. 3B). The tightest binding JAK phosphopeptide was that from JAK-3 with an $IC_{50}$ value of 110 μM, however, this affinity is 1,000-fold weaker than for gp130(750-764). The JAK2-derived peptide bound SOCS-3 with even lower affinity, some 10,000-fold weaker than gp130(750-764). The observed affinities of the JAK-derived peptides for SOCS-3 seem inordinately weak for an SH2 domain binding to a phosphopeptide ligand derived from a biologically-relevant target. Based on this binding data, it seems far more likely that pY757 on gp130 is the physiological site of SOCS-3 interaction, and not the activation loop on the JAK kinases.

EXAMPLE 9 pY757 is Important for Inhibition of gp130 Signaling by SOCS-3

The peptide studies indicated that tyrosine 757 was likely to be the preferred binding site for the SOCS-3 SH2 domain and consequently have an important role in the specificity and mechanism of SOCS-3 action. It was therefore important to confirm these findings using a biological assay. A chimeric receptor was created that contained the erythropoietin receptor (EPOR) extracellular domain and the gp130 cytoplasmic domain (EPOR/gp130). A second receptor was created containing the EPO receptor extracellular domain and the gp130 cytoplasmic domain in which tyrosine 757 had been mutated to phenylalanine (EPOR/gp130Y757F). 293T cells were transiently transfected with cDNAs expressing the receptor constructs and either SOCS-3 or SOCS-1 in the presence of the APRE-luc and Srα-β-gal reporter genes. Cells were then incubated in the presence of 10U/ml EPO overnight and luciferase activity determined. Mutation of Y757 in the gp130 cytoplasmic domain has been reported to result in a hyperactive receptor complex, presumably from the loss of a negative regulator such as SHP-2. These results are consistent with these observations as EPO activation of the EPOR/gp130Y757F receptor resulted in a four-fold higher level of luciferase activity than activation of the EPO/gp130 receptor. When high levels of SOCS DNA were transfected (170 ng), SOCS-3 inhibited both EPOR/gp130 and EPOR/gp130Y757F equally. However, SOCS-3 was able to inhibit the wild-type gp130 cytoplasmic domain (EPOR/gp130) at much lower concentrations of DNA than the mutated gp130 cytoplasmic domain (EPOR/gp130Y757F) (50% inhibition at 4 ng compared with 54 ng SOCS-3 DNA). This difference was not observed when SOCS-1 DNA was used and strongly suggests that SOCS-3 acts by binding to gp130 tyrosine 757 When SOCS-3 is highly over-expressed, i.e. when 170 ng DNA is transfected, it is likely that the levels of SOCS-3 protein are saturating and SOCS-3 also inhibits signaling by binding to members of the JAK family in a non-specific manner.

EXAMPLE 10

SOCS-3 Recognizes an Extended Epitope on gp130

SH2 domains recognize tyrosine phosphorylated polypeptides as ligands. While a central phosphotyrosine residue is the primary binding determinant, other amino acids within the immediate vicinity of the phosphotyrosine residue also contribute to the specificity of the association. For prototypical SH2 domains, such as that from src, the sidechains of the 1st (pY+1) and 3rd (pY+3) amino acid residues downstream from the phosphotyrosine residue contribute to the overall protein-ligand association by interacting with specific residues within the SH2 domain. More generally, 2 or 3 of the amino acids between the pY+1 and pY+5 residues contribute to SH2 binding, while residues upstream from pY do not participate in binding interactions.

To better understand the structural basis of SOCS-3 ligand binding specificity, a series of gp130(750-764) phosphopeptide analogues were synthesized. These analogues were either truncated or contained single alanine substitutions relative to the gp130 (750-764) parent phosphopeptide. The affinities of these peptides for SOCS-3 was measured in the competitive binding assay, and compared to that of the gp130 (750-764) phosphopeptide (Table 2). Based on the data from this series of peptides, the side chains of at least 5 non-phosphotyrosine residues appear to be interacting with SOCS-3, these being the pY-1 and -2 residues, in addition to pY-+3, +4 and +5. While it is possible that the pY+1 and +2 sidechains also participate in interactions with SOCS-3. This is not apparent from the alanine substitution data. Thus, compared to most other SH2 domains SOCS-3 recognizes an extended polypeptide epitope and this interaction includes ligand residues that are N- and C-terminal to phosphotyrosine.

TABLE 2

$IC_{50}$ values for gp 130(750-764) phosphopeptide and analogues

| Peptide | $IC_{50}$ (nM) | $IC_{50}$ analogue/ $IC_{50}$ wild-type |
|---|---|---|
| STASTVE(pY)STVVHSG [SEQ ID NO:8] | 110 | |
| STASTVE(pY)ATVVHSG [SEQ ID NO:9] | 72 | 0.65 |
| STASTVE(pY)SAVVHSG [SEQ ID NO:10] | 110 | 1.0 |
| STASTVE(pY)STAVHSG [SEQ ID NO:11] | 3400 | 31 |
| STASTVE(pY)STVAHSG [SEQ ID NO:12] | 1100 | 10 |
| STASTVE(pY)STVVASG [SEQ ID NO:13] | 770 | 7.0 |
| STASTVE(Y)STVVHSG [SEQ ID NO:14] | $2.0 \times 10^6$ | 18,000 |
| STASTVE(pY)STVVHS [SEQ ID NO:15] | 61 | 0.55 |
| STASTVE(pY)STVVH [SEQ ID NO:16] | 77 | 0.70 |
| STASTVE(pY)STVV [SEQ ID NO: 17] | 1100 | 10 |
| AcTVE(pY)STVVHSG [SEQ ID NO:18] | 120 | 1.1 |
| AcVE(pY)STVVHSG [SEQ ID NO:19] | 110 | 1.0 |
| AcE(pY)STVVHSG [SEQ ID NO:20] | 970 | 8.8 |
| Ac(pY)STVVHSG [SEQ ID NO:21] | 9600 | 87 |
| AcAE(pY)STVVHSG [SEQ ID NO:22] | 580 | 5.3 |
| AcVA(pY)STVVHSG [SEQ ID NO:23] | 550 | 5.0 |

EXAMPLE 11

Effects of Binding of SOCS-3 to gp130, EPO and Leptin

SOCS-3 regulates signaling by binding to the intracellular region of the receptor subunit gp130 when tyrosine (757) is phosphorylated. Docking of SOCS to the receptor inhibits the binding of other signaling proteins to the receptor, preventing signal transduction.

The present example shows that there are critical residues within the sequence of the phospho-tyrosine peptide of gp130 that SOCS-3 specifically binds. These residues along with the phospho-tyrosine can be used to identify key signaling regions on other cytokine receptors. Examples of these can be found for both leptin receptor and erythropoietin (EPO) receptor (FIG. 5).

Specific binding of the EPO and Leptin receptor phosphotyrosine peptides to SOCS-3 can be demonstrated using the biosensor as described in Example 4. Briefly, biotinylated gp130 (Y757), EPO and leptin peptides (FIG. 5) are immobilized to a streptavidin chip on the biosensor. A gp130 phospho-tyrosine peptide (Y681; FNSKDQM(pY)SDGN-FTD) is also coupled to the sensorchip to serve as a control. Simultaneous binding of SOCS-3 (100 nM) to mgp130, EPO and leptin phospho-tyrosine peptides and control peptide can be monitored on a Biacore 2000. Subtraction of the control sensorgram from the other channels demonstrates specificity of the signal.

Figure 6:
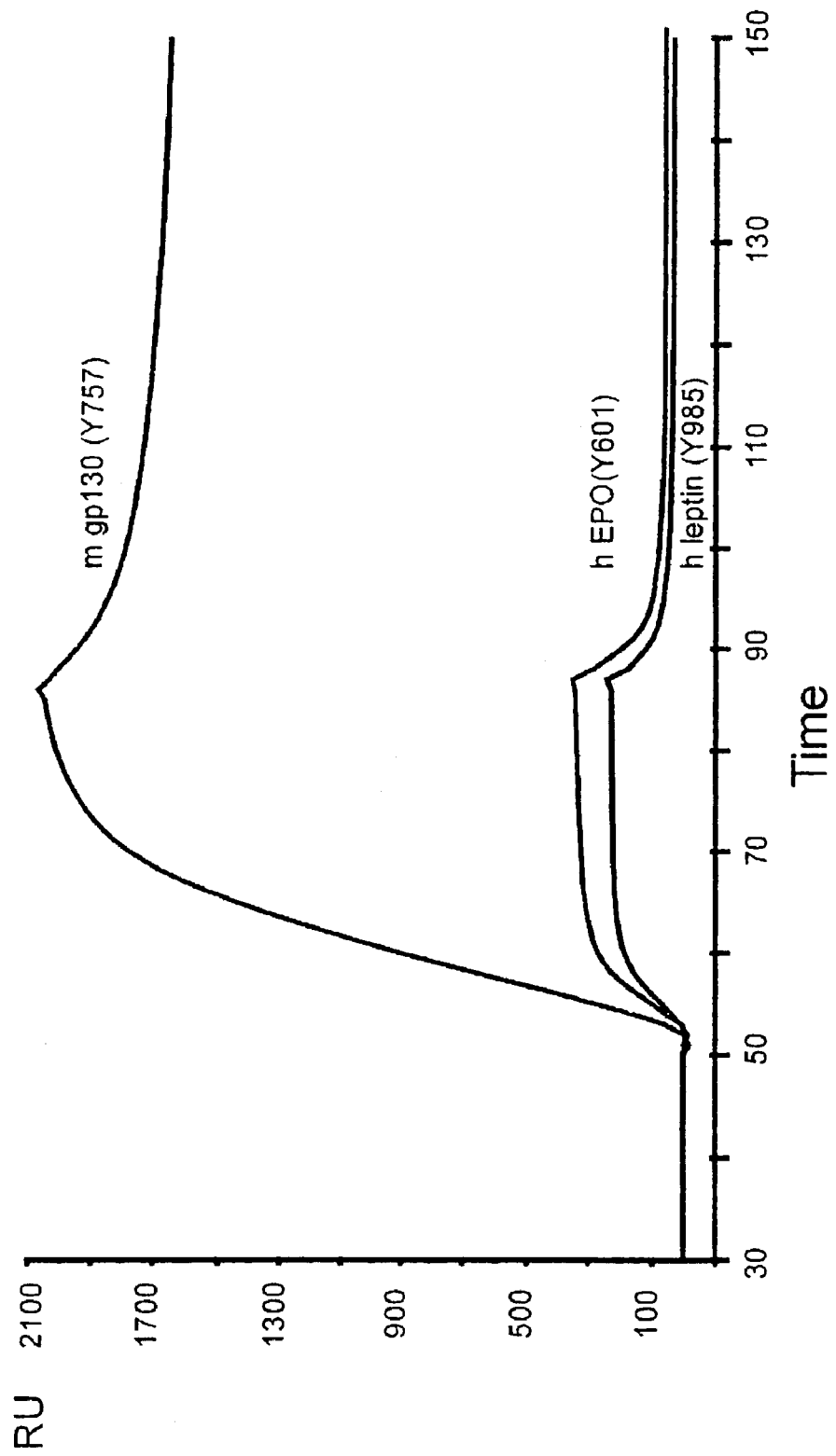
FIG. 6 is a graphical representation of human SOCS-3 binding to the phosphopeptides murine gp130 (pY757) human EPO (pY601) and human leptin (pY985).

The binding of SOCS-3 to these peptides is shown (FIG. 6). These interactions form the basis for a high throughput molecular screen designed to identify antagonists of the interaction of SOCS-3 with both the EPO and leptin receptors.

BIBLIOGRAPHY

Adams et al. (1999) *J Biol Chem* 273:1285-1287
Auernhammer, C. J. and Melmed, S. (1999) *Endocrinology* 140: 1559-1566
Bjorbaek et al. (1999) *Endocrinology* 140: 2035-2043
Bjorbaek et al. (1999) *J Biol Chem* 274: 30059-30065
Bjorbaek et al. (1998) *Mol Cell* 1: 619-625
Bousquet et al. (1999) *J Clin Invest* 104: 1277-1285
Cohney et al. (1999) *Mol Cell Biol* 19: 4980-4988
Donnelly et al. (1999) *J Interferon Cytokine Res* 19: 563-573
Endo et al. (1997) *Nature* 387: 921-924
Gisselbrecht, S. (1999) *Eur Cytokine Netw* 10: 463-470
Hansen et al. (1999) *Mol Endocrinol* 13: 1832-1843
Heim, M. H. (1999) *J Recept Signal Transduct Res* 19: 75-120
Hilton, D. J. (1999) *Cell Mol Life Sci* 55: 1568-1577
Hilton et al. (1998) *Proc Natl Acad Sci USA* 95: 114-119
Ihle (1998) *Ann NY Acad Sci* 865:1-9
Ito et al. (1999) *Blood* 93: 1456-1463
Kamura et al. (1998) *Genes Dev* 12: 3872-3881
Leonard, W. J. and O'Shea, J. J. (1998) *Annu Rev Immunol* 16: 293-322
Marine et al. (1999) *Cell* 98: 617-627
Masuhara et al. (1997) *Biochem Biophys Res Commun* 239: 439-446
Matsumoto et al. (1997) *Blood* 89: 3148-3154
Minamoto et al. (1997) *Biochem Biophys Res Commun* 237: 79-83
Naka et al. (1997) *Nature* 387: 924-929
Narazaki et al. (1998) *Proc Natl Acad Sci USA* 95: 13130-13134
Nicholson, S. E. and Hilton, D. J. (1998) *J Leukoc Biol* 63: 665-668
Nicholson et al. (1999) *EMBO J.* 18: 375-385
Ogilvy et al. (1998) *Blood* 91: 419-430
Pezet et al. (1999) *J Biol Chem* 274: 24497-24502
Sasaki et al. (1999) *Genes Cells* 4: 339-351
Starr et al. (1997) *Nature* 387: 917-921
Suzuki et al. (1998) *Oncogene* 17: 2271-2278
Yasukawa et al. (1999) *EMBO J* 18: 1309-1320
Yoshimura, A. (1998) *Leukemia* 12: 1851-1857
Yoshimura et al. (1995) *EMBO J* 14: 2816-2826
Zhang et al. (1999) *Proc Natl Acad Sci USA* 96: 2071-2076

The invention claimed is:

1. A method for identifying a modulator of interaction between a human or murine SOCS-3 molecule and a gp130 receptor, said method comprising:

immobilizing said SOCS-3 molecule or a part thereof to a solid support, wherein said part comprises the SH2 domain of said SOCS-3 molecule;

contacting the immobilized SOCS-3 molecule or the part thereof with said gp130 receptor or a part of said gp130 receptor in the presence of a potential agonist or antagonist, wherein said part of said gp130 receptor comprises the cytoplasmic domain of said gp130 receptor or at least SEQ ID NO:5; and measuring qualitatively or quantitatively a change in binding between said SOCS-3 or said part of said SCOS-3 and said gp130 receptor or said part of said gp130 receptor, as compared to binding in the absence of said potential agonist or antagonist, thereby identifying a modulator of interaction between said SOCS-3 molecule and said gp130 receptor.

2. The method of claim 1, wherein the immobilization of said SOCS-3 molecule or said part of said SOCS-3 is achieved via binding partners, wherein one of said binding partners is attached to said solid support and another of said binding partners is linked to said SOCS-3 molecule or said part of said SOCS-3 and the two binding partners bind to each other.

3. A method for identifying a modulator of interaction between a human or murine SOCS-3 molecule and a gp130 receptor, said method comprising:

immobilizing said gp130 receptor or a part thereof to a solid support, wherein said part comprises the cytoplasmic domain of said gp130 receptor or at least SEQ ID NO:5;

contacting the immobilized gp130 receptor or said part thereof with said SOCS-3 molecule or a part of said SOCS-3 in the presence of a potential agonist or antagonist, wherein said part of said SOCS-3 comprises the SH2 domain of said SOCS-3; and measuring qualitatively or quantitatively a change in binding between said SOCS-3 or said part of said SOCS-3 and said gp130 receptor or said part of said gp130 receptor, as compared to binding in the absence of said potential agonist or antagonist, thereby identifying a modulator of interaction between said SOCS-3 molecule and said gp130 receptor.

4. The method of claim 3, wherein immobilization of said gp130 receptor or said part of said gp130 receptor is achieved via binding partners, wherein one of said binding partners is attached to said solid support and another of said binding partners is linked to said gp130 receptor or said part of said gp130 receptor and two binding partners bind to each other.

5. A method according to any one of claims 1-4, wherein the SOCS-3 molecule or the part thereof interacts with a region of the gp130 receptor comprising a phosphorylated tyrosine.

6. The method of claim 5, wherein said region of the gp130 receptor comprises the amino acid sequence set forth in SEQ ID NO: 5.

7. A method according to any one of claims 1-4 wherein the solid support is a biochip.

8. A method according to claim 2 or 4 wherein the binding partners are biotin and streptavidin.

9. A method for identifying a modulator of interaction between a human or murine SOCS-3 molecule and a gp130 receptor, said method comprising:

immobilizing said SOCS-3 molecule or a part thereof to a solid support via binding partners comprising biotin and streptavidin, wherein said part comprises the SH2 domain of said SOCS-3 molecule, and wherein one of said biotin or streptavidin is attached to said solid support and the other is linked to said SOCS-3 molecule or said part;

contacting the immobilized SOCS-3 molecule or said part with said gp130 receptor or a part of said gp130 receptor in the presence of a potential agonist or antagonist, wherein said part comprises the cytoplasniic domain of said gp130 receptor or at least SEQ ID NO:5; and measuring qualitatively or quantitatively a change in binding between said SOCS-3 or said part of said SOCS-3 and said gp130 receptor or said part of said gp130 receptor, as compared to binding in the absence of said potential agonist or antagonist, thereby identifying a modulator of interaction between said SOCS-3 molecule and said gp130 receptor.

10. The method of claim 9, wherein streptavidin is attached to said solid support and biotin is linked to said SOCS-3 molecule or said part of said SOCS-3 molecule.

11. The method of claim 9, wherein biotin is attached to said solid support and streptavidin is linked to said SOCS-3 molecule or said part of said SOCS-3 molecule.

12. A method of identifying a modulator of interaction between a human or murine SOCS-3 molecule and a gp130 receptor, said method comprising:

immobilizing said gp130 receptor or a part thereof to a solid support via binding partners comprising biotin and streptavidin, wherein said part comprises the cytoplasmic domain of said gp130 receptor or at least SEQ ID NO:5, and wherein one of said biotin or streptavidin is attached to said solid support and the other of said biotin or streptavidin is linked to said gp130 receptor or said part thereof;

contacting the immobilized gp130 receptor or said part thereof with said SOCS-3 molecule or a part of said SOCS-3 molecule in the presence of a potential agonist or antagonist, wherein said part of said SOCS-3 molecule comprises the SH2 domain of said SOCS-3 molecule; and measuring qualitatively or quantitatively a change in binding between said SOCS-3 or said part of said SOCS-3 and said gp130 receptor or said part of said gp130 receptor, as compared to binding in the absence of said potential agonist or antagonist, thereby identifying a modulator of interaction between said SOCS-3 molecule and said gp130 receptor.

13. The method of claim 12, wherein streptavidin is attached to said solid support and biofin is linked to said gp130 receptor or said part of said gp130 receptor.

14. The method of claim 12, wherein biotin is attached to said solid support and streptavidin is linked to said gp130 receptor or said part of said gp130 receptor.

15. A method according to any one of claims 9, 10, 12, 13, or 11 wherein the SOCS-3 molecule or the part thereof interacts with a region of the gp130 receptor comprising a phosphorylated tyrosine.

16. The method of claim 15 wherein said region of the gp130 receptor comprises the amino acid sequence set forth in SEQ ID NO: 5.

17. A method according to any one of claims 9, 10, 12, 13, or 14 wherein the solid support is a biochip.

* * * * *